US008828004B2

(12) United States Patent
Nakamura

(10) Patent No.: US 8,828,004 B2
(45) Date of Patent: Sep. 9, 2014

(54) SURGICAL CHISEL

(76) Inventor: Shu Nakamura, Inuyama (JP)

( * ) Notice: Subject to any disclaimer, the term of this patent is extended or adjusted under 35 U.S.C. 154(b) by 368 days.

(21) Appl. No.: 13/127,198

(22) Filed: May 2, 2011

(65) Prior Publication Data

US 2011/0213370 A1 Sep. 1, 2011

Related U.S. Application Data

(63) Continuation of application No. PCT/JP2009/068082, filed on Oct. 13, 2009.

(30) Foreign Application Priority Data

Nov. 6, 2008 (JP) .................................. 2008-309109

(51) Int. Cl.
A61B 17/16 (2006.01)

(52) U.S. Cl.
CPC ......... *A61B 17/1604* (2013.01); *A61B 17/1657* (2013.01); *A61B 17/1671* (2013.01)
USPC .......................................................... 606/83

(58) Field of Classification Search
USPC .......... 606/79–85, 86 R, 96–99, 100; 173/90; 30/167, 168; 81/20
See application file for complete search history.

(56) References Cited

U.S. PATENT DOCUMENTS

| 4,979,574 | A | * | 12/1990 | Lalama et al. | ..................... | 173/1 |
| 6,126,664 | A | * | 10/2000 | Troxell et al. | .................. | 606/84 |
| 6,423,073 | B2 | * | 7/2002 | Bowman | ....................... | 606/104 |
| 2001/0027322 | A1 | | 10/2001 | Bowman | | |

FOREIGN PATENT DOCUMENTS

| EP | 1234545 A2 | 8/2002 |
| JP | 62-189708 U | 12/1987 |
| JP | 5-063511 U | 8/1993 |
| JP | 2002-535031 A | 10/2002 |
| JP | 2002-355254 A | 12/2002 |
| WO | 00/42924 A1 | 7/2000 |

OTHER PUBLICATIONS

International Search Report of PCT/JP2009/068082, mailing date Nov. 24, 2009.

* cited by examiner

*Primary Examiner* — Christopher Beccia
(74) *Attorney, Agent, or Firm* — Westerman, Hattori, Daniels & Adrian, LLP

(57) ABSTRACT

A chisel includes a hammered portion to be hammered which is provided so as to project from a middle or an end of a handle and extend to pass through a portion on an extended line in the direction opposite to the direction of the blade. Even if the chisel is hammered in a state where a tip of the blade thereof is not inserted into a bone, the chisel easily advances in the direction of the blade, thereby reducing a possibility that the blade slides on a surface of the bone.

4 Claims, 5 Drawing Sheets

SURGICAL CHISEL

This application claims the benefit of priority to International Patent Application No. PCT/JP2009/068082 filed Oct. 13, 2009 claiming priority upon Japanese Patent Application No. 2008-309109 filed Nov. 6, 2008, of which full contents are incorporated herein by reference.

BACKGROUND OF THE INVENTION

1. Field of the Invention

The present invention relates to an angled chisel used for cutting a bone of a lumbar spine in minimally invasive surgery for lumbar spinal canal stenosis.

2. Description of the Related Art

FIG. 1 is an axial cross-sectional view illustrating a normal lumbar spinal canal. A lumbar spinal canal 1 is a lumen surrounded by a facet joint 2, a ligamentum flavum 3, a vertebral arch 4, an intervertebral disc, and the like. A spinal cord, a dura mater, and nerve roots run in the lumbar spinal canal 1. The lumbar spinal canal stenosis is a disease which causes neurological symptoms in legs by narrowing of the spinal canal due to hypertrophy of the facet joint, hyperplasy of the ligamentum flavum, or the like as illustrated in FIG. 2.

Posterior decompression which is common as a surgery treatment for the lumbar spinal canal stenosis is a therapeutic approach in which bones of the vertebral arch and the facet joint are partially excised and the ligamentum flavum is also excised so as to expand the spinal canal. As such posterior decompression, an operative procedure which is recently spread as the minimally invasive surgery is a micro endoscopic discectomy (MED). The MED is an operative procedure in which a tubular retractor having a diameter of slightly smaller than 2 cm is installed at the backside of the vertebral arch and the surgery is completed in the tubular retractor under an endoscope. A spinous process and a supraspinous ligament are important as lumbar spine posterior stabilizing mechanisms. With the MED, these tissues can be conserved and invasion of muscles around these tissues can be minimized.

In the MED, an operation is performed in an inner side of a tubular retractor 5 which is an elongated tube as illustrated in FIG. 2. Therefore, a surgical region is limited by an angle and a position of the tubular retractor. An upper portion of the tubular retractor cannot be inclined to the side of a spinous process 6 due to obstruction of the spinous process 6 at the approach side. Therefore, there has been a problem that an angle at which a medial facet is cut at the approach side is as indicated by a solid line 7 and decompression at the approach side cannot be sufficiently made unless extensive bone is excised. Further, if too much bone is excised, many portions of the facet joint are removed or facet fracture is caused. This causes a risk that instability is increased.

In order to conserve the facet bone as indicated by bone-cutting lines of dashed lines 8 as much as possible, it is ideal that a bone is cut outward so as to excise the medial facet at the approach side more selectively. In order to achieve such an object, a chisel of which blade is bent with respect to a handle is already present. However, as a user hammers the chisel so as to advance the chisel, the chisel does not advance in the direction of the bending blade and slides in many cases.

This is because a point 10 to be hammered is located not on an extended line 12 in the direction opposite to the direction of the blade 11 but on an end of a handle 9 for gripping on the chisel as illustrated in FIG. 3. If the chisel is hammered in a state where a tip of the blade thereof is not inserted into a bone, the chisel advances on a line 13 connecting the tip of the chisel and the point 10. That is, in such a case, the chisel does not advance in the direction of the blade and slides on a surface of the bone.

SUMMARY OF THE INVENTION

In order to solve the above problem, an object of the invention is to provide a chisel for cutting a bone easily in the direction of a blade on an angled chisel used when a bone of a lumbar spine is cut in minimally invasive surgery for lumbar spinal canal stenosis.

A surgical chisel includes a blade, a handle having a gripping portion, and a hammered portion to be hammered as a main structure. The blade is bent with respect to the handle. Further, the hammered portion is arranged so as to project from the handle and extend to pass through a portion on an extended line opposite to the direction of the blade.

DETAILED DESCRIPTION OF THE INVENTION

Figure 1:
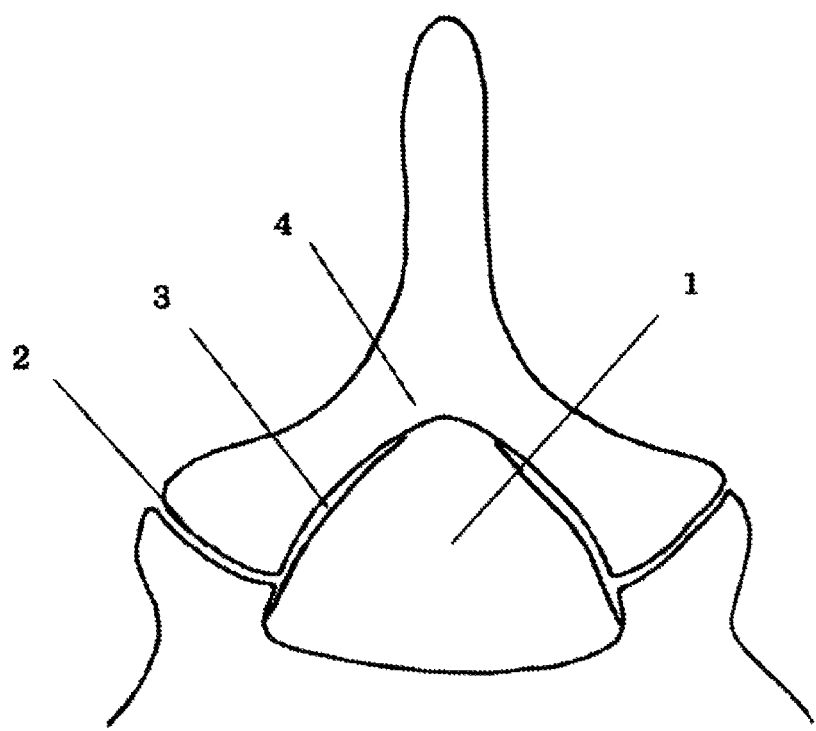
FIG. 1 is a cross-sectional view illustrating a normal lumbar spinal canal.
Figure 2:
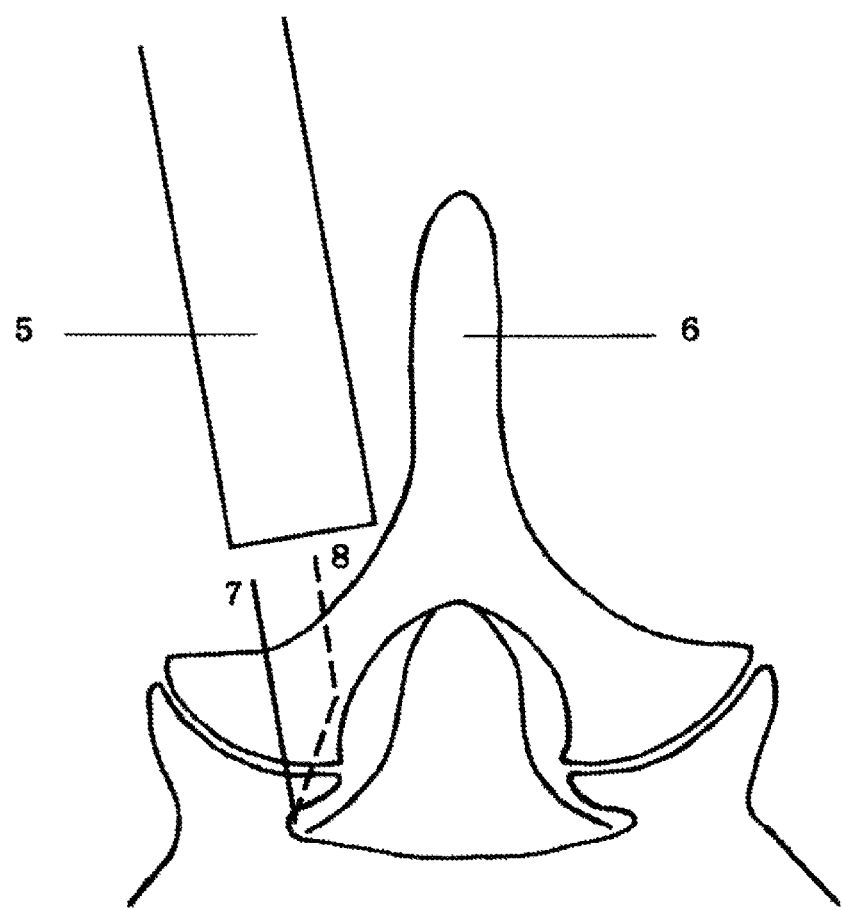
FIG. 2 is a cross-sectional view illustrating a spinal canal of lumbar spinal canal stenosis.
Figure 3:
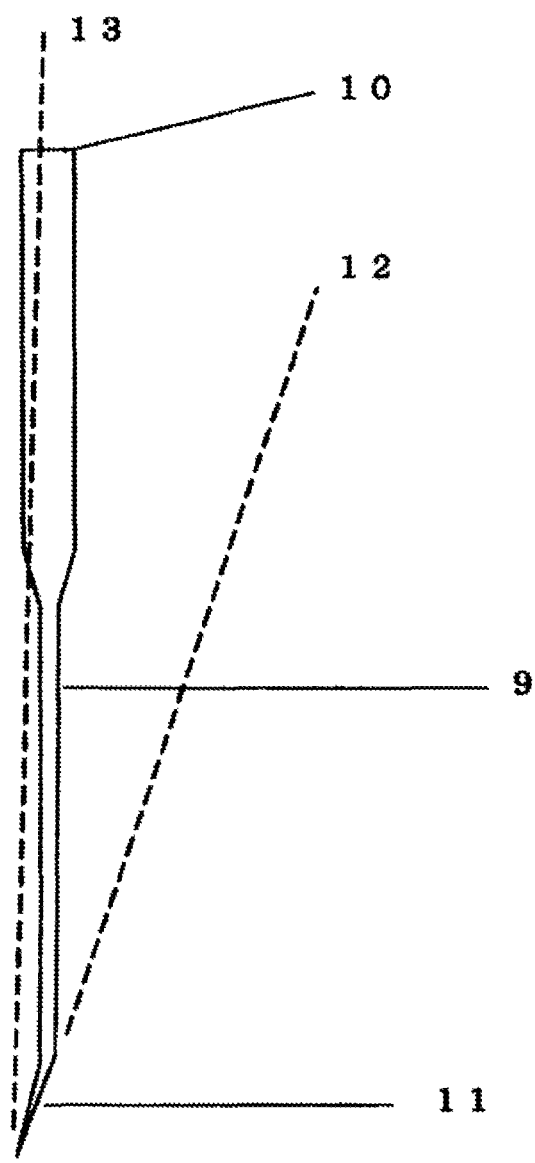
FIG. 3 is a side view illustrating a conventional angled chisel.
Figure 4:
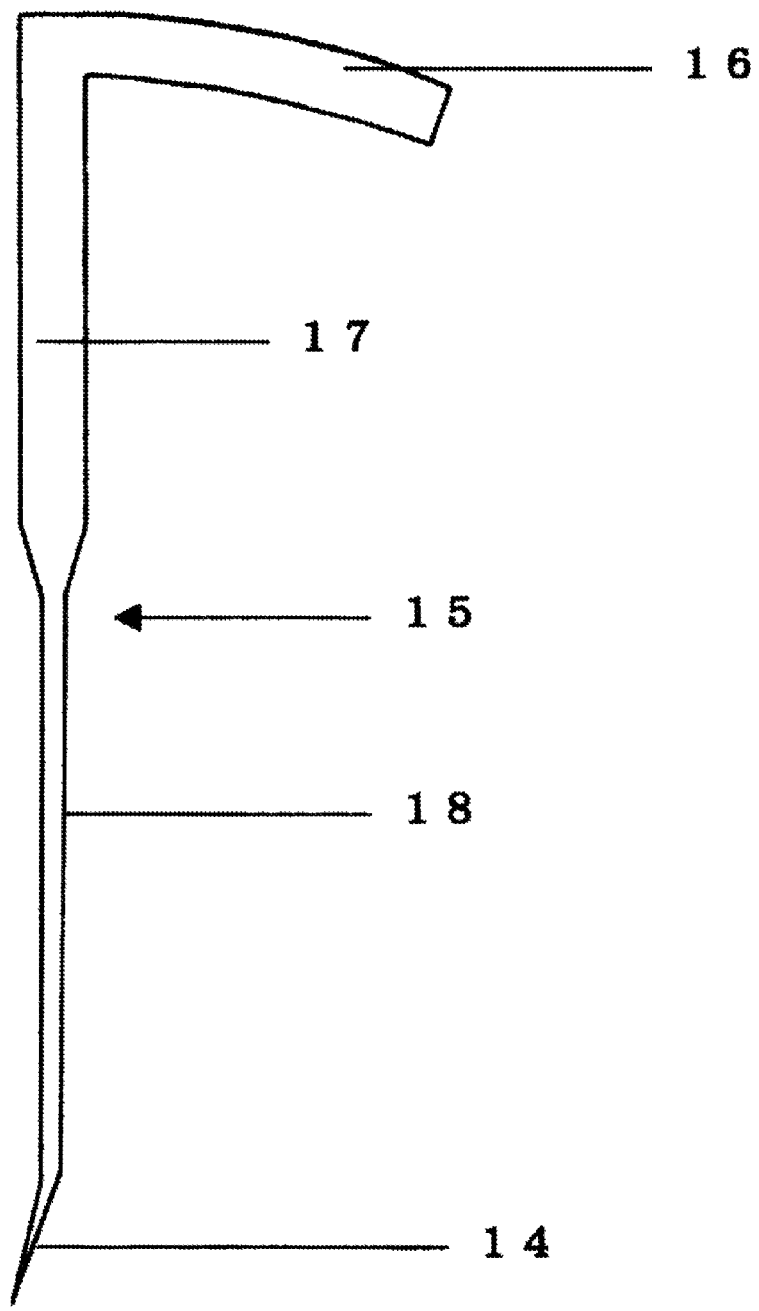
FIG. 4 is a side view according to a reference example.

A reference example is described with reference to FIG. 4. As illustrated in FIG. 4, a chisel includes a blade 14, a handle 15 for gripping, and a hammered portion 16 to be hammered as a main structure. The blade 14 is bent with respect to the handle 15. The handle 15 is constituted by a grip 17 and a shaft 18. The grip 17 is a portion which is made thick for being gripped by hand. The shaft 18 is continuous to the blade 14. The hammered portion 16 is a hard structure which is continuous to an end of the handle 15 in a bending manner. Further, the hammered portion 16 has an arc shape as drawn about a tip of the blade 14 as a center point and has such length that the hammered portion 16 passes through a portion on an extended line in the direction opposite to direction of the blade.

If a portion of the hammered portion 16, which corresponds to a portion on the extended line in the direction opposite to the direction of the blade, is hammered, the chisel tends to advance in the direction of the blade. The direction in which the blade advances can be finely adjusted as follows. That is, the hammered portion 16 is hammered at the further tip side when a surface of a bone is hard so that the blade easily slides. Or the hammered portion 16 is hammered at the further handle side when a user desires to advance the chisel in the axial direction of the handle.

Figure 5:
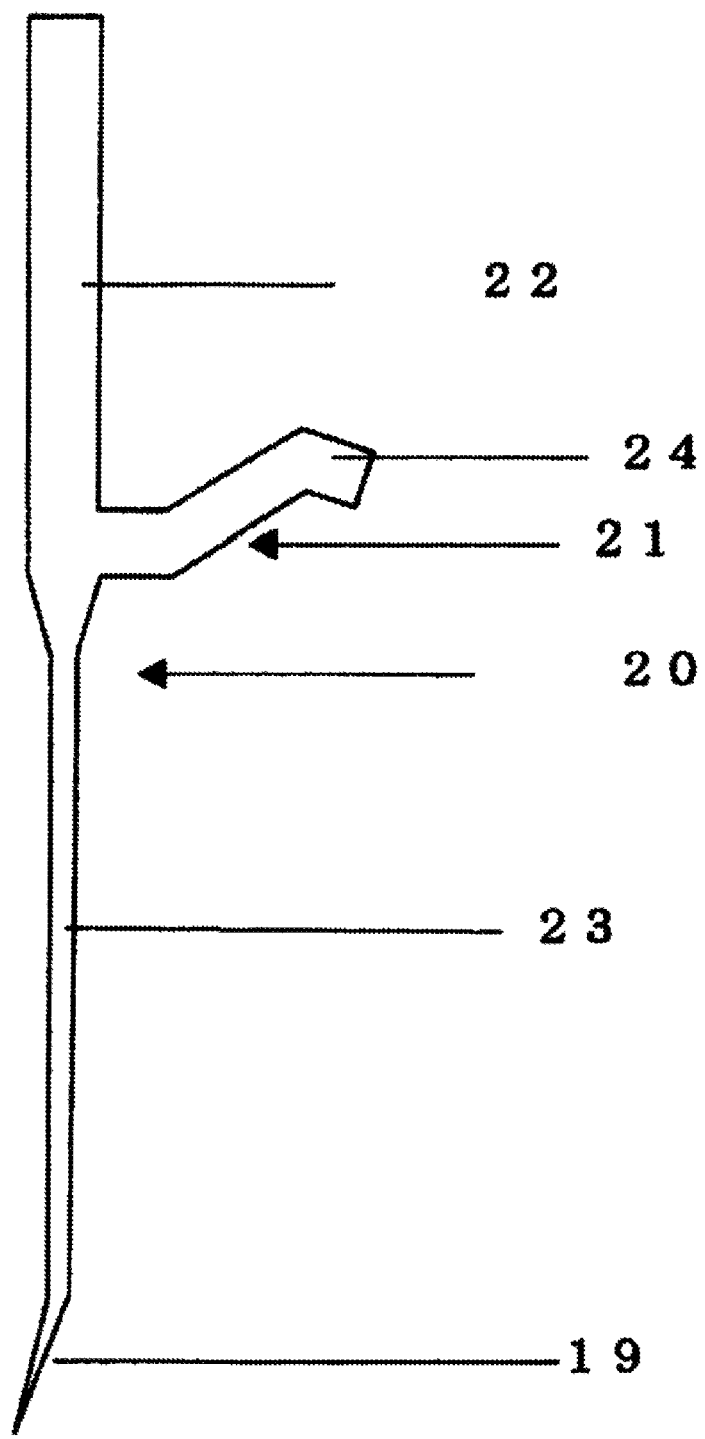
FIG. 5 is a side view according to a preferred embodiment of the invention.

A preferred embodiment of the invention is described with reference to FIG. 5. A chisel includes a blade 19, a handle 20 for gripping, and a hammered portion 21 to be hammered as a main structure. The blade 19 is bent with respect to the handle 20. The handle 20 is constituted by a grip 22 and a shaft 23. The grip 22 is a portion which is made thick for being gripped by hand. The shaft 23 is continuous to the blade 19. The hammered portion 21 is a hard structure which is branched from a lower end of the grip 22 of the handle 20 so as to extend in the direction opposite to the bending direction of the blade 19. Further, a hammered point 24 is attached to the hammered portion 21 near a portion on an extended line in the direction opposite to direction of the blade.

EFFECT OF THE INVENTION

A point to be hammered is located near a portion on a straight line of the direction of the blade. Therefore, even if the chisel is hammered in a state where a tip of the blade thereof is not inserted into the bone, the chisel easily advances in the direction of the blade, thereby reducing a possibility that the blade slides on a surface of the bone.

Therefore, a bone can be cut outward so as to excise the medial facet at the approach side more selectively. Therefore, bones and joints can be conserved as much as possible.

What is claimed is:

1. A surgical chisel comprising:
    a handle including a shaft and a grip, the shaft and the grip being co-axial;
    a blade which is provided at a tip of the shaft and bent with respect to the handle; and
    a hammered portion which is branched from a lower end of the grip,
    wherein, in side view, the hammered portion and the blade extend in opposite lateral directions with respect to the axis of the shaft and the grip, and
    wherein the grip is thicker than the shaft.
2. The surgical chisel according to claim 1,
    wherein, in side view, a hammered point at an end of the hammered portion extends toward a line corresponding to the longitudinal axis of the blade.
3. The surgical chisel according to claim 1,
    wherein an entirety of the grip is thicker than the shaft, and
    wherein the hammered portion is branched from a point proximal to a transition point between the grip and the shaft.
4. The surgical chisel according to claim 1,
    wherein the hammered portion is integral with the grip.

* * * * *